June 11, 1974 W. A. WARRINER Plant Pat. 3,569
ROSE PLANT
Filed Aug. 14, 1972
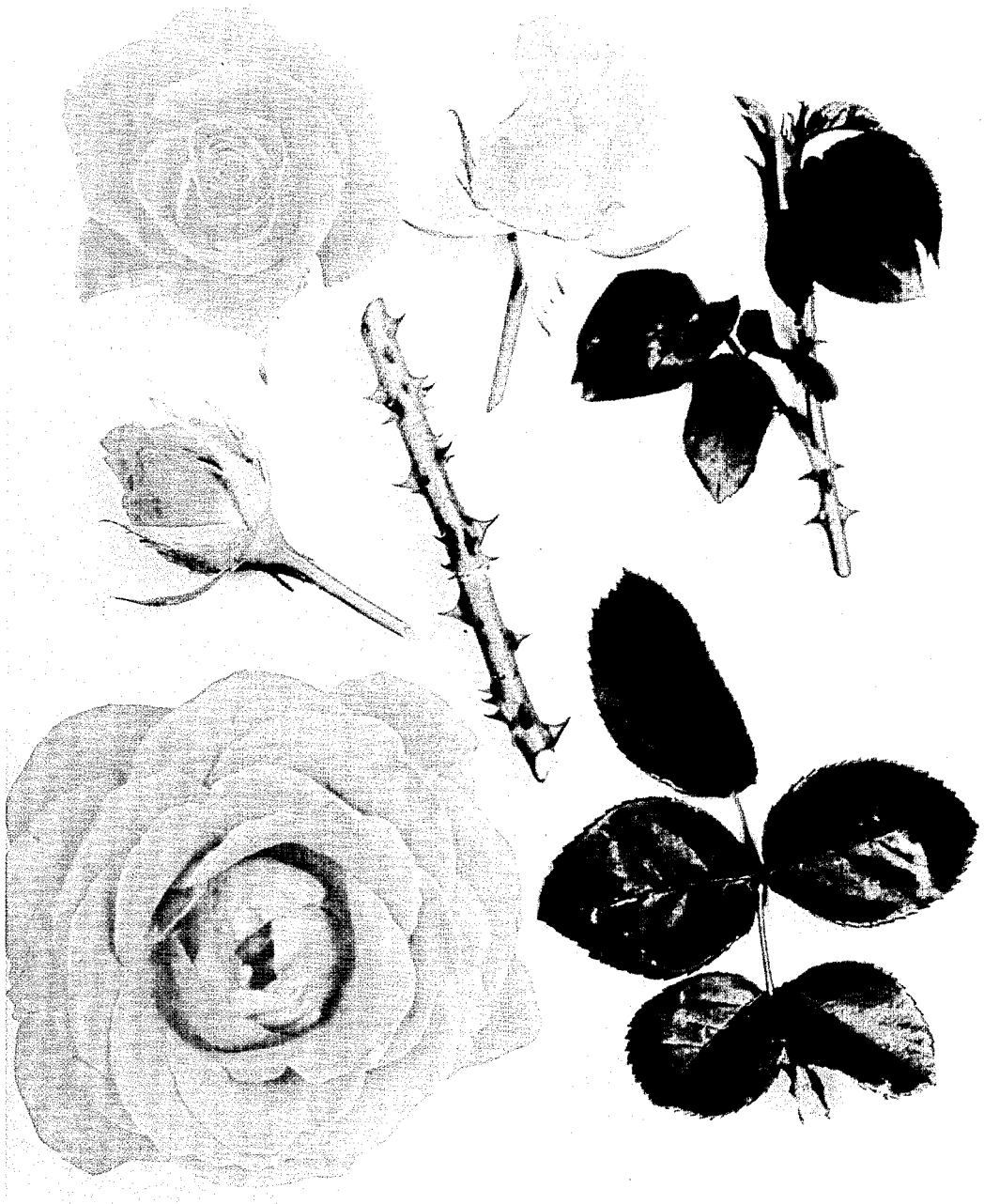

United States Patent Office

Plant Pat. 3,569
Patented June 11, 1974

3,569
ROSE PLANT

William A. Warriner, Tustin, Calif., assignor to Jackson & Perkins Company, Medford, Oreg.

Filed Aug. 14, 1972, Ser. No. 280,537
Int. Cl. A01h 5/00
U.S. Cl. Plt.—17 1 Claim The present invention relates to a new and distinct variety of rose plant of the hybrid tea class which was originated by me by crossing two unnamed seedlings.

The primary objective of this breeding was to produce a new rose variety of very vigorous character bearing near red or orange red blooms and having foilage very resistant to affects of rose powdery mildew.

This objective was subst antially achieved along with other desirable improvements as evidenced by the following unique combinations of characteristics which are outstanding in the new variety and which distinguish it from its parents as well as from all other varieties of which I am aware:

1. A very vigorous habit of growth.
2. An unusual amount of basal shoots produced, thereby providing many growing points and a great many flowers.
3. Basal shoots terminate in long-stemmed (12"–14") clusters of six or more blooms.
4. Secondary or lateral shoots usually produce blooms singly.
5. A "semi-double" flower of 23 to 30 petals, usually in the low twenties.
6. Color very close to Wilson's Dutch Vermillion which holds well from bud to old flower.
7. Very little fragrance.
8. Usually is unaffected by rose powderey mildew.

Asexual reproduction of this new variety by budding, as performed at Wasco, Calif., proves that the foregoing characteristics and distinctions reproduce true to form and are established and transmitted through succeeding propagations.

The accompanying drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significane of color is indicated.

Parentage: Seedling
*Seed parent.*—Seedling of independence × Siren.
*Pollen parent.*—Unnamed seedling.
Classification:
*Botanic.*—*Rosa hybrid.*
*Commercial.*—*Hybrid tea.*

FLOWER

Observations were made at Irvine, Calif., in May 1972 in the afternoon.

Blooming habit: Recurrent—continuous.
Bud:
*Size.*—1½ inches when petals start to unfurl.
*Form.*—Long, pointed.
*Color.*—When sepals first divide near Blood Red (820). When half blown; inside of petals slightly darker and slightly more red than Dutch Vermillion (717), at point of attachment, a very small area of Lemon Yellow (4/1), reverse of petals near Geranium Lake (20).

*Sepals.*—Color: Outer surface—Scheeles Green (860/3) heavily overlaid in irregular areas with a color lighter than Garnet Brown (00918/3). Inner surface—Lighter than outer surface, covered with fine, white tomentum. Three appendaged sepals lightly appendaged. Two unappendaged sepals smooth edged. Numerous stipitate glands on outer surface of sepals.
*Receptacle.*—Color: Scheeles Green (860/3). Shape: Funnel. Size: Small. Surface: Smooth.
*Peduncle.*—Length: Short. Surface: Prickly, glandular. Color: Light green, lighter than Garnet Brown on side exposed to sun. Strength: Bending, slender.
*Opening.*—Spiral type, petals curl slightly on edges.
Bloom:
*Size.*—Large. Average size when fully expanded, 4–4½ inches. Larger in early spring.
*Borne.*—Singly and several together.
*Stems.*—Long and medium, normal strength.
*Form.*—When first open, high centered. Permanence—flattens, outer petal edges slightly curled.
*Petalage.*—Number of petals under normal, conditions about 25.
*Color.*—Center of flower: Upper side of petals Dutch Vermillion (717). Reverse side of petals Signal Red (179/3). Outer petals: Upper side of petals same as center petals. Base of petals: Small area at point of attachment Lemon Yellow (4/1). (General tonality from a distance Dutch Vermillion (717). No variegations.
*Discoloration.*—General tonality at end of first day Dutch Vermillion (717). By third day only slightly lighter.
*Fragrance.*—Very little.
Petals:
*Texture.*—Thick.
*Surface.*—Inside—satiny. Reverse—satiny.
*Shape.*—Round.
*Form.*—Tips slightly recurved.
*Arrangement.*—Loosely imbricated.
*Petaloids in center.*—Few.
*Persistance.*—Drop off cleanly.
*Lastingness.*—On the plant—long. As cut flower—long.
Reproductive parts:
*Stamens, anthers.*—Large, many. Color—Chinese Yellow (606). Arrangement—regular around styles.
*Stamens, Filaments (threads).*—Long medium. Color—Fire Red (15/1) with Lemon Yellow basal one fourth.
*Pollen.*—Lemon Yellow.
*Styles.*—Loosely separated, of uneven lengths, thin.
*Stigmas.*—Color—Amber Yellow (505/2).
*Ovaries.*—All enclosed in calyx.
Fruit: (Not observed.)

PLANT

Form: Bush.
Growth: Very vigorous, upright, branching.
Foliage: Number of leaflets on normal mid-stem leaves, 5 or 7.
*Size.*—Large.
*Quantity.*—Abundant.
*Color.*—New foliage: Garnet Brown (00918/3). Old foliage: near Parsley Green (00962).
Leaflets:
*Shape.*—Elliptical.
*Texture.*—Leathery. Under side rough. Ribs and veins prominent.
*Edge.*—Serrated.

*Serration.*—Single, medium sized.

*Petiole (rachis).*—Color—green. Underside—prickles.

*Stipules.*—Long, mostly adnate with rachis.

*Disease resistance.*—Resistant to mildew under normal growing conditions at Irvine, Calif.

Wood:

*New Wood.*—Color—similar to new foliage, Garnet Brown (00918/3). Bark—smooth.

*Old Wood.*—Color—green. Bark—smooth.

Prickles:

*Quantity.*—On main stalks—many. On laterals—many.

*Form.*—Broad based, hooked downward.

*Color.*—When young—Garnet Brown, also Garnet Brown when old.

*Position.*—Irregular.

Small Prickles:

*Quantity.*—On main stalks—many. On laterals—many.

*Color.*—Brown.

This new variety is further characterized by vigorous basal shoots terminating in large clusters of blooms (6–8) on stems 12 to 14 inches or longer, the basal shoots being produced in abundance.

I claim:

1. A new and distinct variety of rose plant of the hybrid tea class, substantially as herein shown and described, characterized particularly as to novelty by the unique combination of its vigorous growth, abundant basal branching, Dutch Vermillion blooms, and its resistance to rose powdery mildew.

No references cited.

ROBERT E. BAGWILL, Primary Examiner